United States Patent [19]

Shorr

[11] Patent Number: 5,679,736
[45] Date of Patent: Oct. 21, 1997

[54] ADDITIVE FIRE RETARDANTS, PROCESS FOR THEIR PREPARATION AND POLYMERIC COMPOSITIONS CONTAINING THEM

[75] Inventor: Leonard Shorr, Haifa, Israel

[73] Assignee: Bromine Compounds Limited, Beer-Sheva, Israel

[21] Appl. No.: 62,129

[22] Filed: May 17, 1993

[30] Foreign Application Priority Data

May 18, 1992 [IL] Israel ......................... 101913

[51] Int. Cl.$^6$ ................... C08K 5/03; C08K 3/10
[52] U.S. Cl. ................ 524/464; 524/467; 524/411; 570/183; 570/206; 570/208
[58] Field of Search ................... 570/183, 206, 570/208; 524/464, 467, 411

[56] References Cited

U.S. PATENT DOCUMENTS

| | | | |
|---|---|---|---|
| 2,552,607 | 5/1951 | Warner | 570/183 |
| 2,552,608 | 5/1951 | Warner | 570/183 |
| 3,161,692 | 12/1964 | McLaughlin et al. | 570/200 |
| 3,270,068 | 8/1966 | van Venrooy et al. | 570/183 |
| 3,923,866 | 12/1975 | Sawa et al. | 570/183 |
| 4,988,785 | 1/1991 | Paul et al. | 526/259 |

FOREIGN PATENT DOCUMENTS

| | | |
|---|---|---|
| AL-138766 | 4/1985 | European Pat. Off. |
| 963931 | 7/1950 | France . |
| 917783 | 9/1954 | Germany . |
| 65101 | 5/1948 | Netherlands . |
| 651528 | 4/1951 | United Kingdom . |
| AM-651528 | 4/1951 | United Kingdom . |

OTHER PUBLICATIONS

AR–Chemical Abstracts, vol. 104 (1986), 33903r "Substituted 1–phenylindanes" Stegman, et alX (see Reference AL, above).

Primary Examiner—Kriellion S. Morgan
Attorney, Agent, or Firm—Michael N. Meller

[57] ABSTRACT

Novel fire retardant compounds are disclosed, which are poly-halogenated TMPI and MPI compounds containing three or more halogen atoms per molecule. A process for the preparation of these compounds and polymeric compositions containing them are also described.

16 Claims, 19 Drawing Sheets

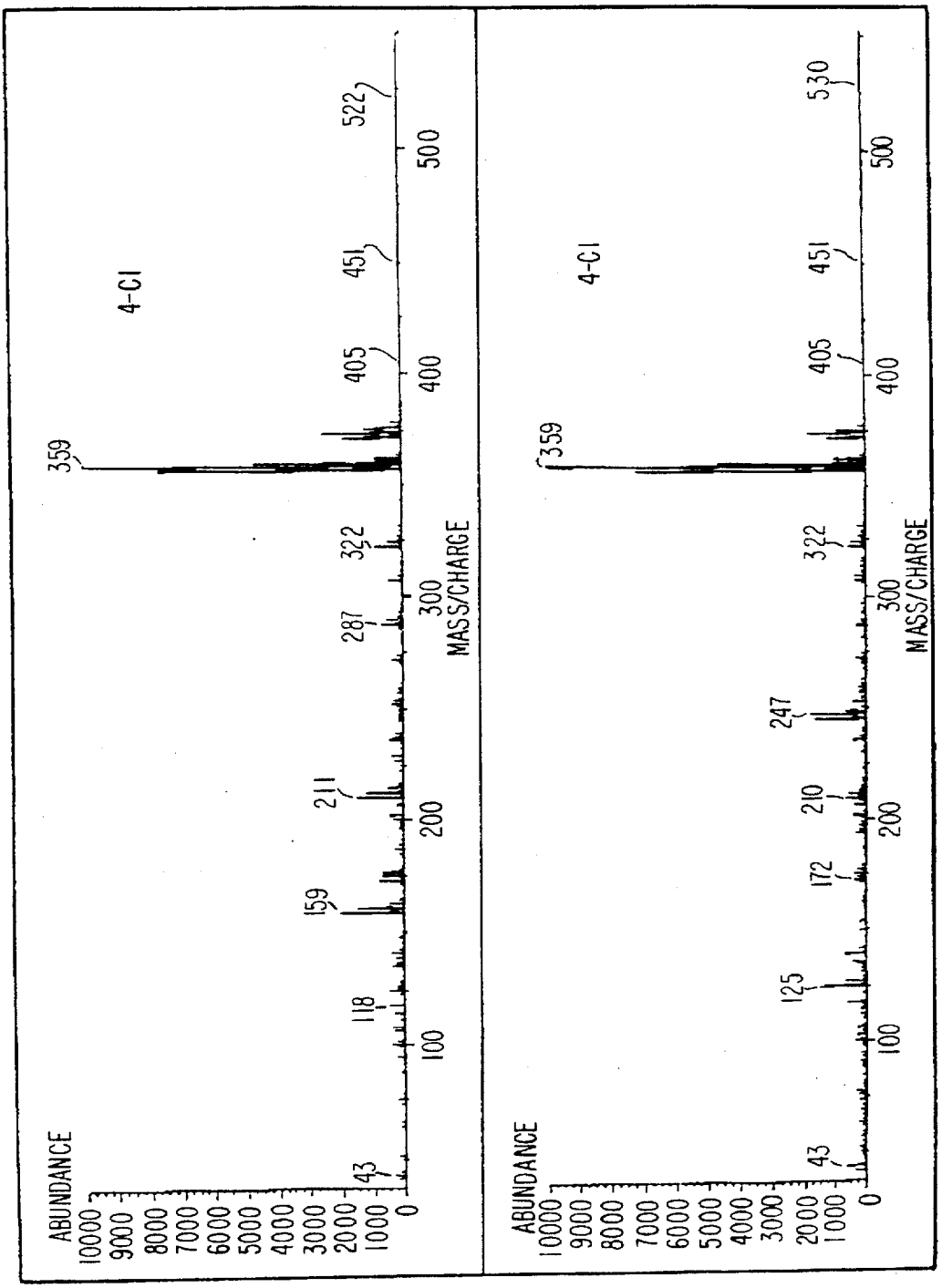

ADDITIVE FIRE RETARDANTS, PROCESS FOR THEIR PREPARATION AND POLYMERIC COMPOSITIONS CONTAINING THEM

FIELD OF THE INVENTION

This invention refers to additive fire retardants, to processes for their preparation and to polymeric compositions containing them. More specifically, the additive fire retardants are halogenated derivatives of indan, and more specifically halogenated 1,1,3-trimethyl-3-phenyl indan (hereinafter briefly designated as TMPI) and halogenated 1-methyl-3-phenyl indan (hereinafter briefly designated as MPI). Said compounds are useful as fire retardants for a wide spectrum of resins, among them in particular ABS, polyamides, polyolefins, engineering thermoplastics, polyurethanes, and high impact polystyrene (HIPS), rubbers and thermosets. These flame retardants can also be used to produce flame retarded textiles.

BACKGROUND OF THE INVENTION

Fire retardation of polymeric compositions is a widespread requirement and a wide spectrum of fire retardants have been developed. A number of them are halogenated compounds. However fire retarded polymeric compositions, in particular those which contain halogenated fire retardants as additives, suffer from various deficiencies, in particular those due to thermal instability, to poor impact properties and to enhanced sensitivity to ultraviolet light irradiation.

It is a purpose of this invention to provide novel fire retardants which are free from these disadvantages, and in particular are thermally stable, impart good impact properties, and do not impart to polymeric compositions containing them higher sensitivity to ultraviolet irradiation.

It is another purpose of this invention to provide processes for the manufacture of said fire retardants.

It is a further purpose of this invention to provide polymeric compositions which contain said fire retardant as additives and have good mechanical properties, thermal stability and resistance to ultraviolet irradiation.

The fire retardants of this invention are additive fire retardants, and they are derivatives of phenyl indans, more specifically 1-methyl-3-phenyl indan (MPI) and 1,1,3-trimethyl-3-phenyl indan (TMPI). MPI can be obtained by condensing two molecules of styrene. It has been suggested as a starting material for the manufacture of anthraquinone (see Kirk-Othmer, Encyclopedia of Chemical Technology, vol. 3, p.705).

The preparation of TMPI by dimerization of alpha-methylstyrene is disclosed in DE 2,906,294. DE 2,659,597, U.S. Pat. No. 3,161,692 and Petropoulos and Fisher in J. Am. Chem. Soc., 80, 1938 (1958) relate to the dimerization of alpha-methylstyrene and/or ring alkylated alpha-methyl styrenes to yield the corresponding non-halogen containing TMPI compounds. EP 138766 gives an example of the dimerization of 4-chloro-alpha-methylstyrene to produce 6-chloro-1,3,3-trimethyl-1-(4'-chlorophenyl)indan. These products were used as heat transfer fluids and chemical intermediates for polymer manufacture.

U.S. Pat. No. 4,205,160 describes terpolymers of TMPI together with 2,4-diphenyl-4-methyl-2-pentene and 2,4-diphenyl-4-methyl-1-pentene. J. C. Wilson in the Journal of Polymer Science: Polymer Chemistry Edition 13, 749 (1975) describes various TMPI-based polyamides and polyesters. C. W. Paul et al describe in U.S. Pat. No. 4,988,785, resin compositions based on bisphenol compounds which are TMPI derivatives.

SUMMARY OF THE INVENTION

The fire retardant additives according to the invention are characterized in that they are poly-halogenated TMPI and MPI compounds containing three or more halogen atoms per molecule, or mixtures of such compounds.

A process for the preparation of the compounds according to the invention consists in the dimerization of one or more appropriately halogen substituted alpha-methyl styrene or halogen-substituted styrene compounds.

Another, preferred, process for the manufacture of the compounds according to the invention is the ring halogenation of TMPI or MPI.

Said ring halogenation is preferably carried out by reacting the TMPI or MPI substrate with an halogenating agent in an organic solvent in the presence of a catalyst.

The fire retarded polymeric compositions according to the invention comprise a polymeric base and from 0.1 to 60% and preferably from 1 to 40% by weight of a fire retardant additive according to the invention.

Other fire retardants may be added to the polymeric compositions. Among them may be mentioned, by way of example, halogenated or non-halogenated organo-phosphorus compounds, oxides, sulfides or organic salts of antimony, boron or arsenic, zinc borate, magnesium oxide and hydroxide, aluminum trihydrate, as well as other haloorganics, such as decabromodiphenylether, chlorinated polyethylene and chlorinated PVC.

Further, conventional additives may be added to the polymeric compositions according to the invention. These may comprise other fire retardants, antioxidants (such as Irganox), processing aids, (e.g. lubricants), impact modifiers, UV stabilizers (such as Tinuvins), fillers, fiber reinforcements, smoke suppressors and pigments.

DETAILED DESCRIPTION OF PREFERRED EMBODIMENTS

Figure 1:
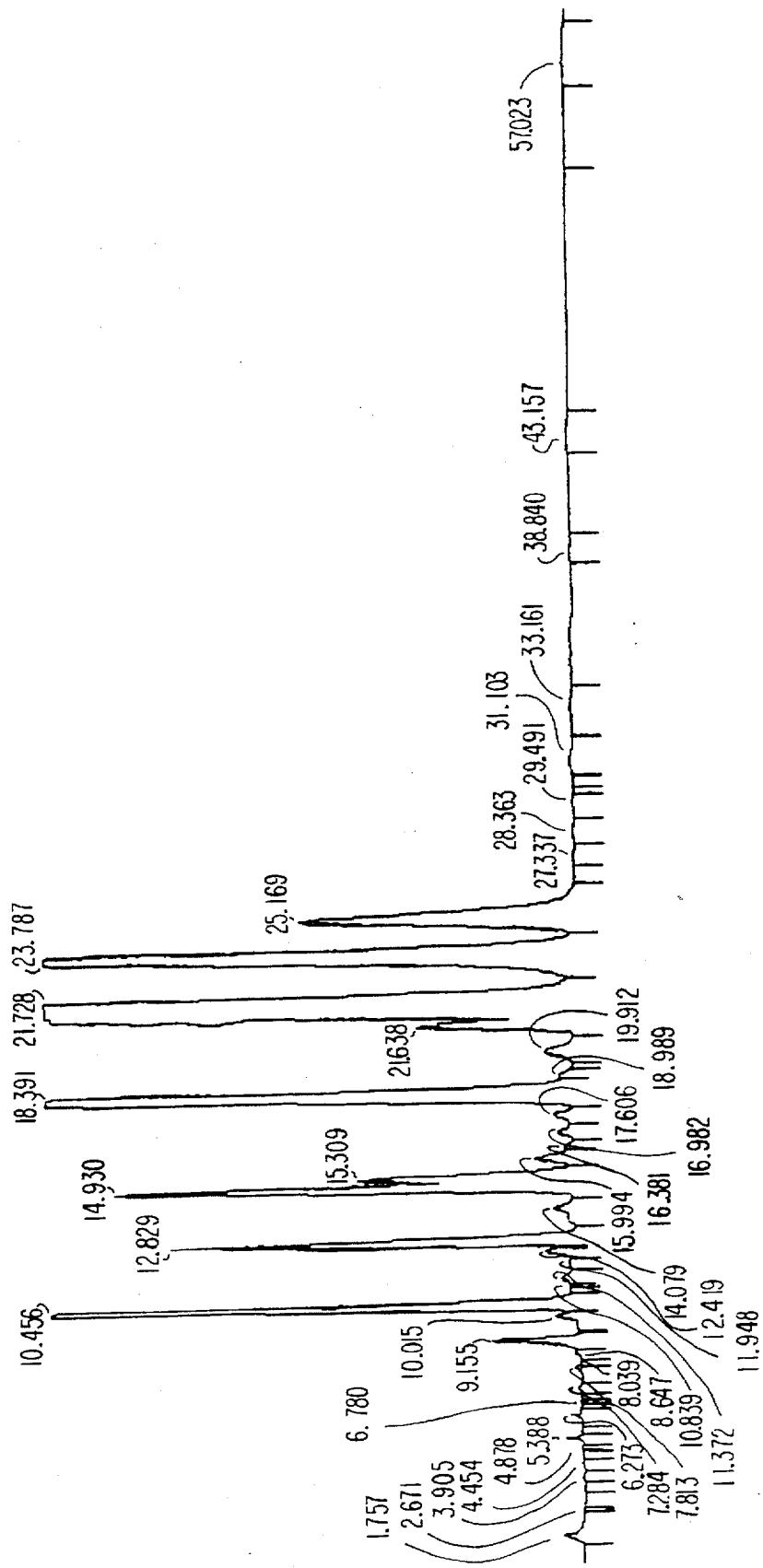
FIGS. 1 to 14 are HPLC chromatograms, TGA analysis graphs, IR spectra and $^1$H NMR spectra characterizing the examples of embodiments of the invention hereinafter described, as specified in each example.

In preparing the fire retardant additives according to the invention by ring halogenation of TMPI or MPI, the preferred halogenation agents are elemental halogens, in particularly bromine and chlorine, but other halogenation agents known in the art, such as bromates, HX (wherein X is Cl or Br) plus hydrogen peroxide etc., can be used. The halogenation is carried out in an organic solvent. The organic solvent medium should be substantially anhydrous and be inert or exhibit low reactivity towards the reactants. Organic solvents free of non-aromatic carbon-to-carbon unsaturation are preferred. Especially useful are halogenated, particularly chlorinated, saturated aliphatic hydrocarbons, such as carbon tetrachloride, chloroform, tetrachloroethane, methylene chloride, trichloroethane, dibromoethane, dibromethane (DBM), and the like. Acetic acid, chlorobenzene and acetonitrile can be used too. Particularly preferred is dibromomethane.

The molar ratio of the halogenating agent to the TMPI or MPI depends on the degree of halogenation desired. A slight excess over stoichiometric ratio is desirable.

The catalyst is preferably a metal or metal halide Lewis acid catalyst, that is capable of effecting the halogenation on the aromatic ring. Examples are the bromides and chlorides of aluminum and iron and mixtures thereof. Specific examples are $AlCl_3$, $AlBr_3$, $FeBr_3$, $SbCl_3$, $SbCl_5$, $SbClBr_4$, $TiCl_4$, $SnCl_2$, $SnCl_4$, $BeCl_2$, $CdCl_2$, $ZnCl_2$, $BF_3$, $BBr_3$, $BCl_3$, $ZrCl_4$. Iodine can also be used. The most preferred catalyst is Fe. The catalysts are used in amounts of at least 1% by weight, based on the weight of indan. Amounts of about 5–10% are preferred. The halogenation is carried out at temperatures comprised between 15° and 100° C., and preferably between 50° and 70° C.

The ring halogenation of TMPI and MPI will generally produce a mixture of compounds having different halogenation degrees, but this is not a drawback because all those compounds are suitable as fire retardant additives. Therefore, when reference is made in this specification to compounds according to the invention, mixtures of such compounds are intended to be included.

The dimerization of styrene derivatives will generally yield a given compound: thus the dimerization of 3,5-dibromo-alpha-methylstyrene will produce 5,7-dibromo-1,3,3-trimethyl-1-(3',5'-dibromophenyl)indan exclusively. The dimerization can be carried out for example as disclosed in EPA 138,766, in the article by L. M. Adams, R. J. Lee and F. T. Wadsworth, J. Org. Chem., 24, 1186 (1959) and in the article by Petropoulos and Fisher hereinbefore cited. However, not all such styrene derivatives are adapted for dimerization, but only those in which at least one ortho position in respect to the alkylene group is free for cyclization to occur.

The fire retardant compounds according to the invention are added to thermoplastic polymers to produce fire retarded polymer compositions by mixing, usually at high temperature, with the polymer. The mixing technique is conventional and can be carried out in conventional equipment without any particular difficulties, especially since the fire retardants according to the invention are highly thermally stable. It is also possible to produce a masterbatch concentrate containing more than 30% of the fire retardant according to the invention, and in some cases synergists; this masterbatch can be diluted in the final resin compositions. When the polymer is a polyurethane, the fire retardants are added to one of its components.

The ring halogenation of TMPI produces compounds having the following general formula I (wherein X is Br or Cl):

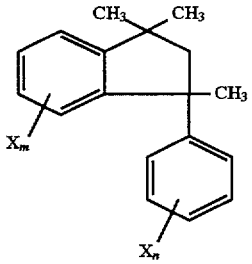
(I)

Similarly, the ring halogenation of MPI produces compounds having the general formula II:

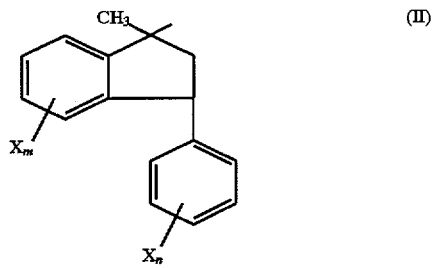
(II)

The degree of halogenation is expressed by the sum: m+n. It is controlled by the molar ratio between the halogenating agent and the TMPI or MPI substrate. It also depends on the concentration (dilution) of the reagents, the temperature and the time of the reaction, and the strength of the catalyst.

TMPI and MPI substituted by three or more halogen atoms are novel compounds. TMPI substituted by two chlorine atoms has been described, as mentioned hereinbefore, in EP 138,766, but its use as fire retardant has not been suggested.

The fire retardant compounds according to the invention not only impart fire retardancy to the polymeric compositions which contain them, but they provide good physico-mechanical properties and resistance to degradation of the products containing them under UV radiation. This latter is a particular surprising feature, since compounds containing high concentrations of halogens, particularly bromine, in their structure, usually promote UV-degradation. Further, the unexpected high thermal stability of the compounds according to the invention makes them particularly suitable for application in engineering thermoplastics.

The unexpected high solubility of the compounds according to the invention (12% in toluene at 100° C.) provides a further advantage of the invention: the reactor and processing utilities can be cleaned of them easily.

A number of embodiments of the invention will now be described.

EXAMPLE 1

Preparation of Partially Brominated TMPI

Into a 3-necked flask (250 ml) equipped with a mechanical stirrer, a reflux condenser and a thermocouple, were added $Br_2$ (35 g; 0.22 mol, 5.5 molar fold over TMPI); Fe (0.75 g; 13.4 mmol) and DBM (100 g). A solution of TMPI (9.45 g, 40 mmol) in DBM (30 g) was added dropwise to the stirred suspension at 35°–65° C. during 2 hrs (the released HBr was trapped in aqueous NaOH). When the reflux of $Br_2$ ceased, water was added to the reaction flask, and the aqueous phase was removed. Then, a solution of $Na_2S_2O_5$ was added to neutralize the residual $Br_2$, and the aqueous phase was removed. Next, water was added again to wash the organic phase, and the aqueous phase was removed. The organic phase was filtered, and the solvent was evaporated. The residue (25 g) solidified. Elementary analysis: found for Br 63.9% (calculated for $C_{18}H_{16}Br_5$ 63.2). The residue consisted of several compounds. The HPLC chromatogram (FIG. 1) showed 3 major peaks.

Figure 2:
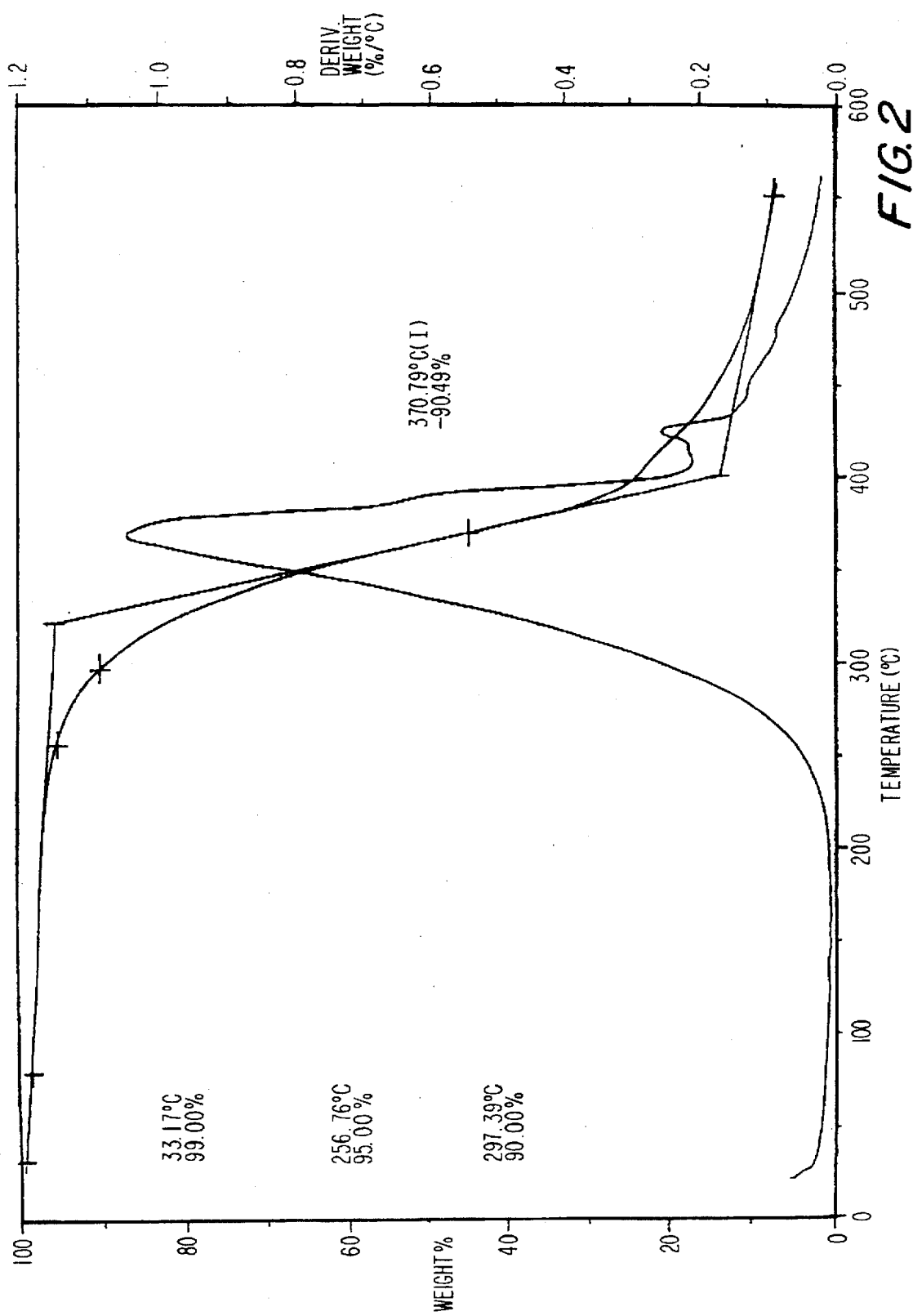

The TGA (FIG. 2) analysis showed a weight loss of 5% at 257° C., 10% at 297° C. and a major peak at 371° C.

Figure 3:
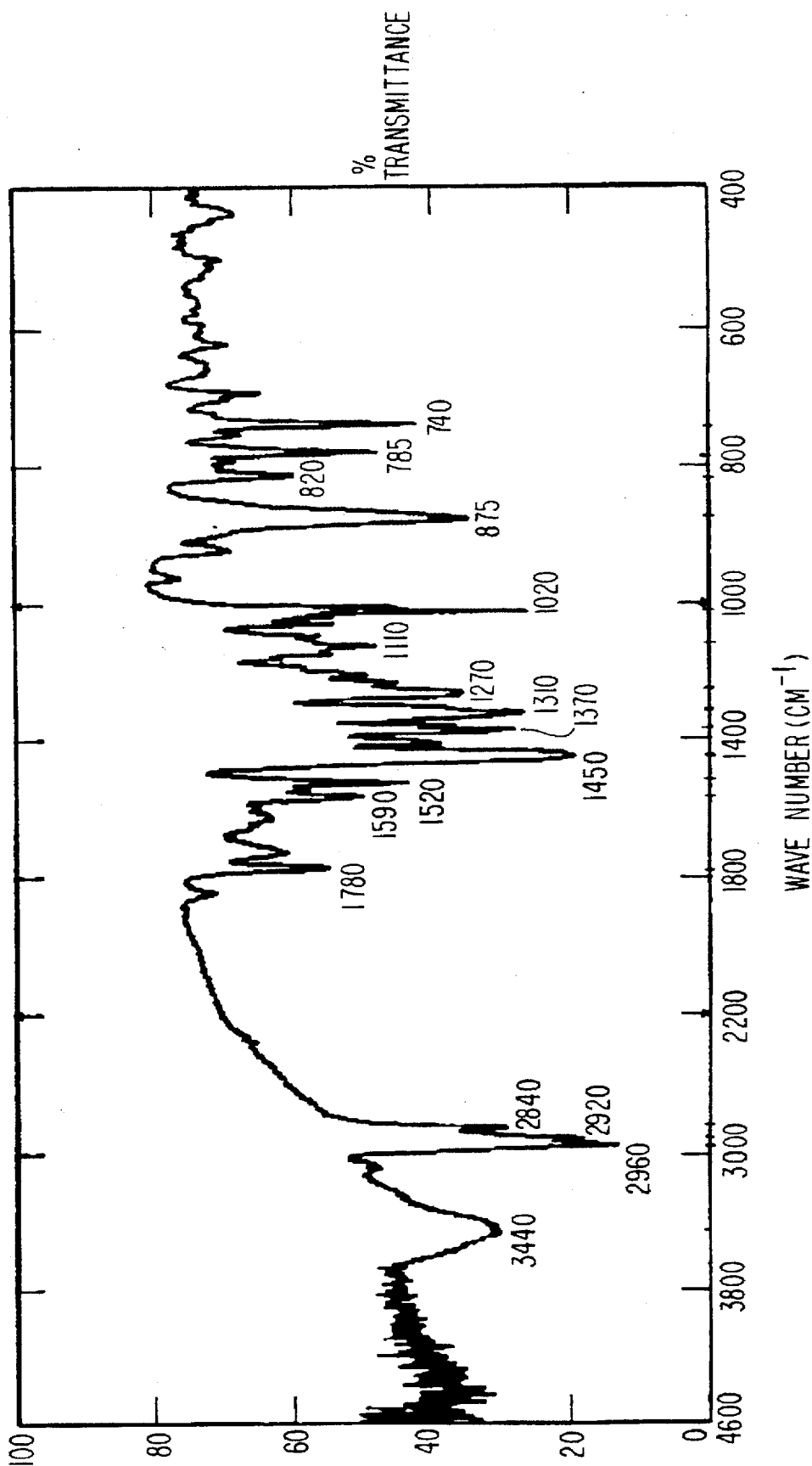

IR (FIG. 3; $cm^{-1}$): 3420, 2960, 2920, 2840, 1780, 1590, 1520, 1450, 1370, 1310, 1270, 1110, 1020, 875, 820, 785, 740.

Figure 4:
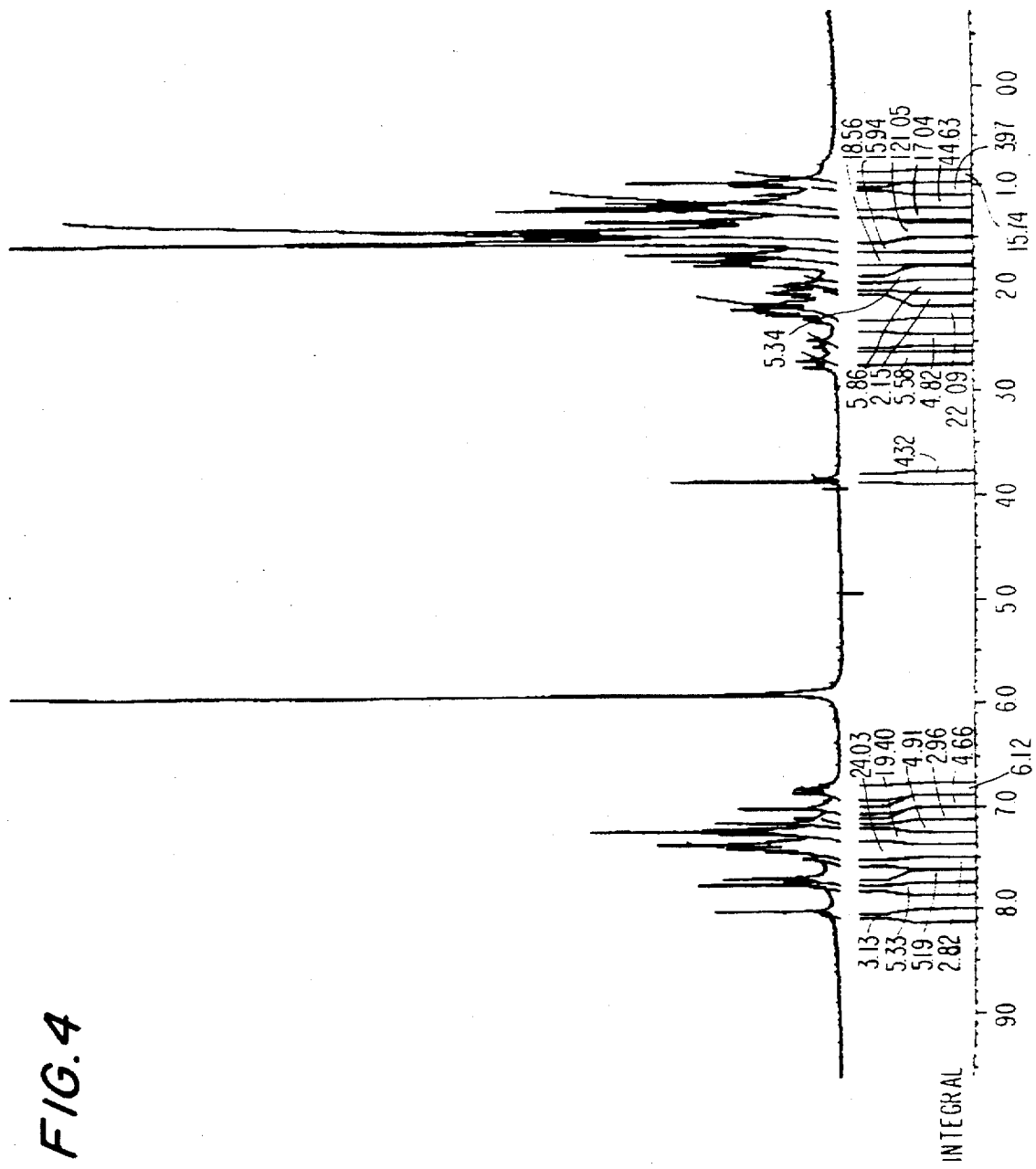

$^1H$ NMR (FIG. 4; δ, in TCE): the spectrum is very complex due to the presence of many isomers in the sample (HPLC spectrum). Three main groups of chemical shifts are characteristic of halogenated TMPI: aromatic hydrogens observed as different singlets (between δ 7 and 8 ppm); the methylenic hydrogens of the cyclopentane ring of the indan observed as AB quartets between δ 2 and 3 ppm; and the methyl groups appearing as sharp peaks between δ 1 and 2 ppm.

EXAMPLE 2

Preparation of Partially Chlorinated TMPI

Into a 3-necked flask (250 ml) equipped with a mechanical stirrer, a reflux condenser and a thermocouple, were added $AlCl_3$ (5.6 g; 42 mmol), $CCl_4$ (130 ml) and TMPI (19.8 g, 84 mmol). $Cl_2$ (30 g; 422 mmol; 5 molar fold over TMPI) was passed into the stirred solution through a diptube (3.5 hrs) at a rate which maintained the reaction temperature of 35°–38° C. (cooling of the reaction mixture with a water bath if necessary). The reflux condenser was cooled to −20° C. (ethylene glycol) in order to avoid losses of $Cl_2$ with the evolution of HCl (the released HCl was trapped in aqueous NaOH). Thirty minutes after the addition of all the $Cl_2$, the evolution of HCl ceased. The reaction mixture was heated to 50° C., and held at that temperature for 30 min. more. The reaction mixture was washed with water (100 ml). Then, a solution of $Na_2S_2O_5$ was added to neutralize the residue of $Cl_2$, and the aqueous phase was removed. Water was added again to wash the organic phase, and the aqueous phase was removed. The organic phase was treated with active carbon, filtered and the solvent was evaporated. A brown oily layer was obtained (23.5 g). Elementary analysis found: C 52.1; H 4.2 and Cl 42.3% (for comparison purposes only, the values calculated for $C_{18}H_{16}Cl_5$ are: C 52.8; H 3.9; Cl 43.3%).

Figure 5:
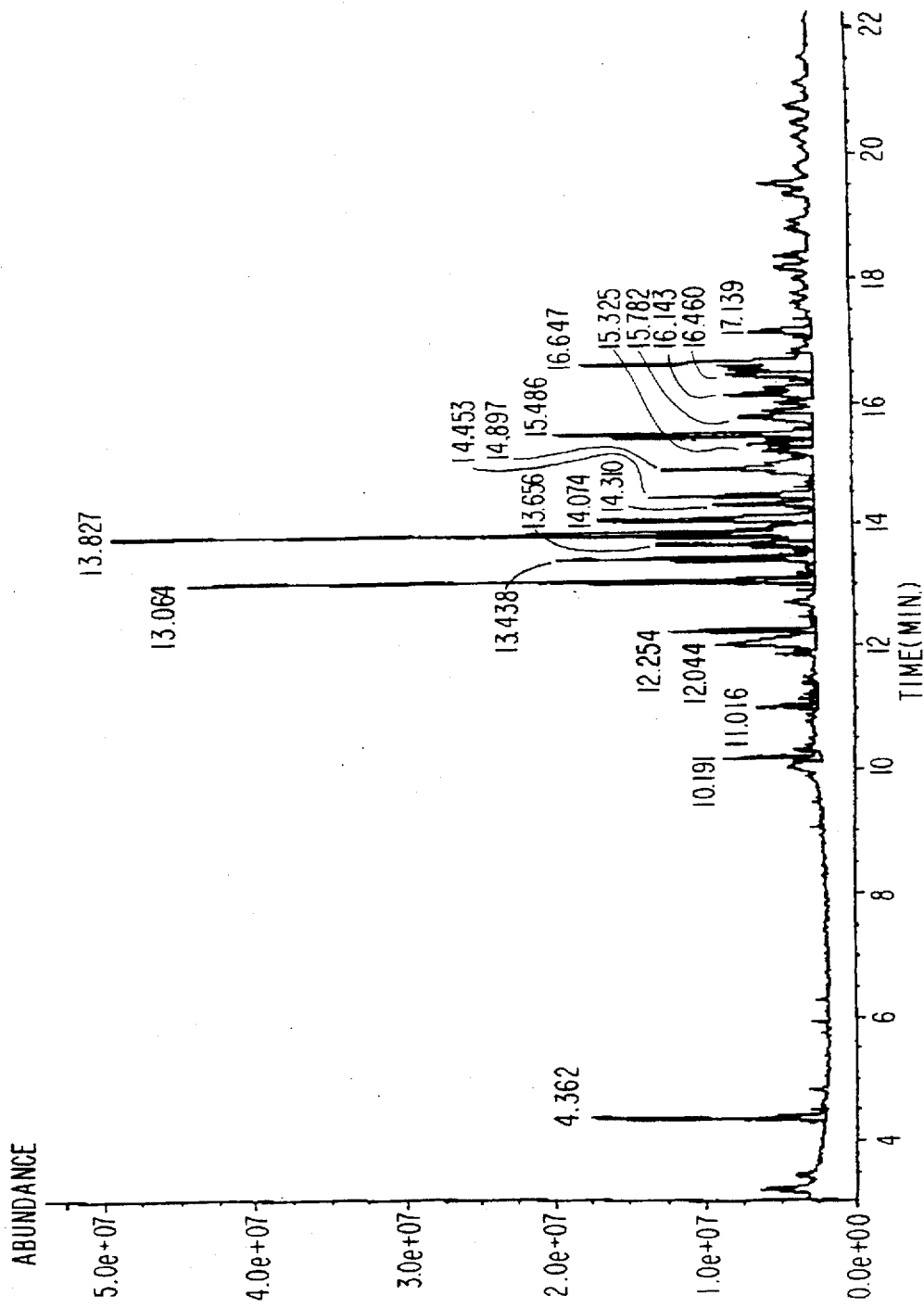
Figure 6A:
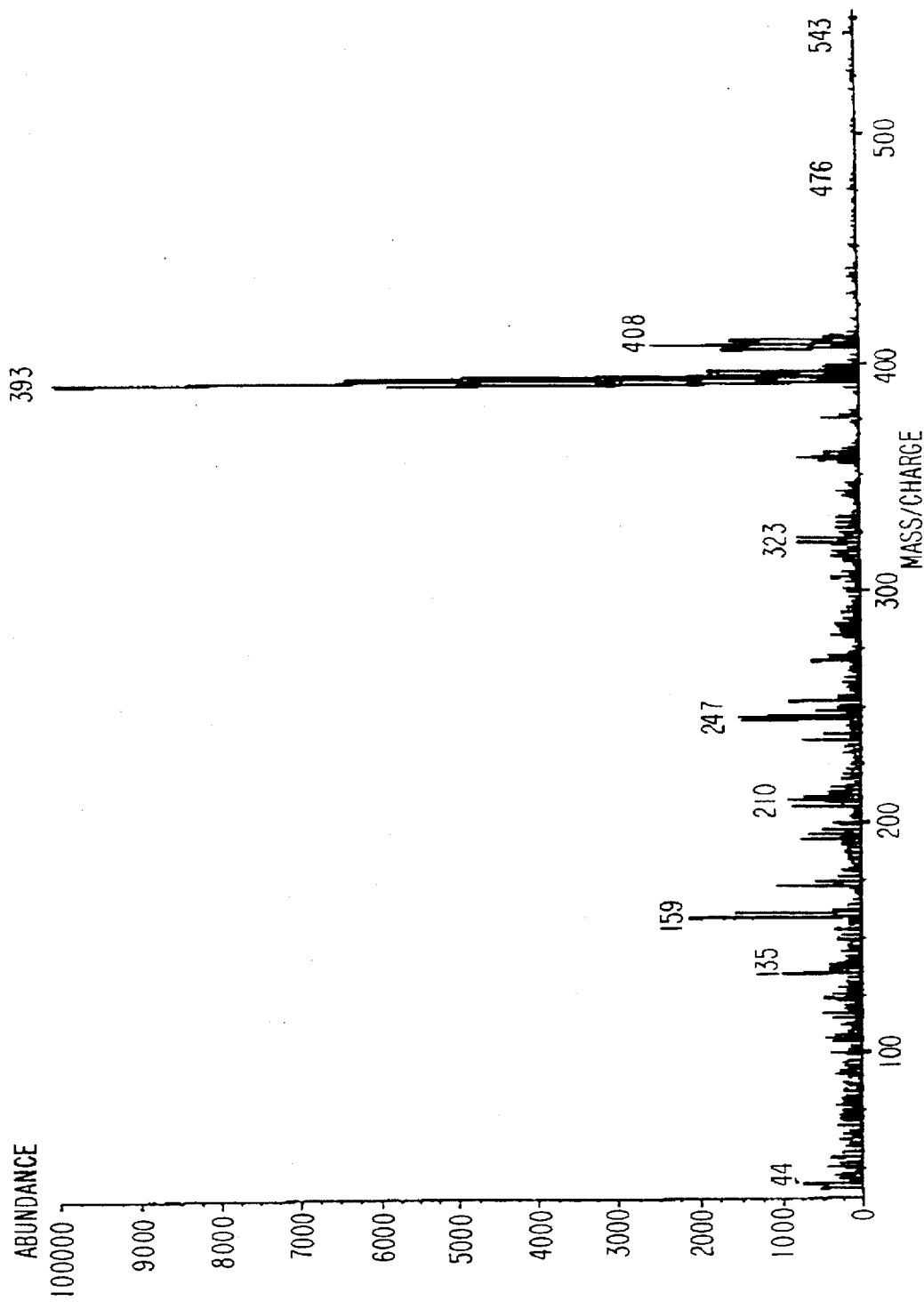
Figure 6B:
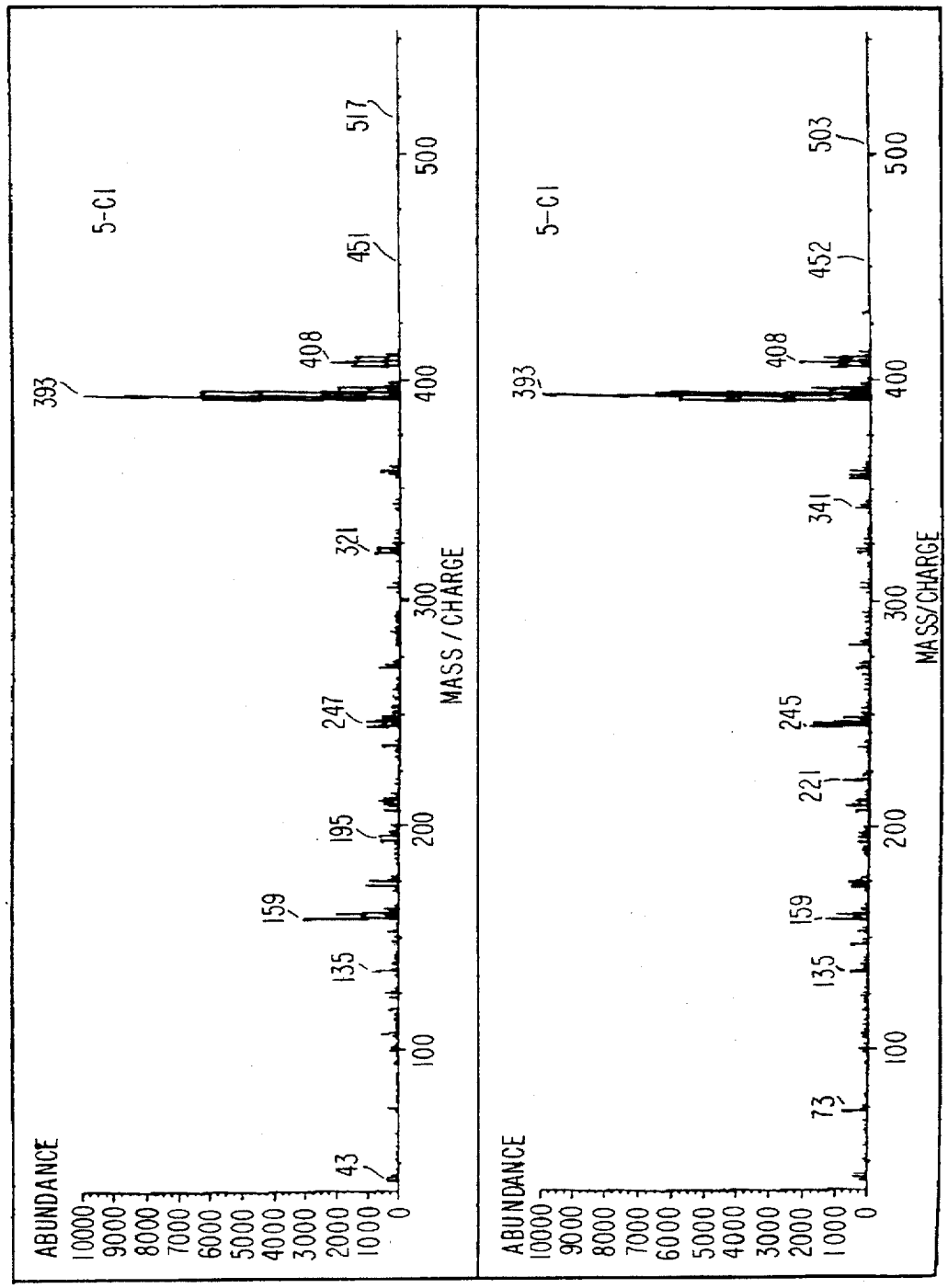
Figure 6C:
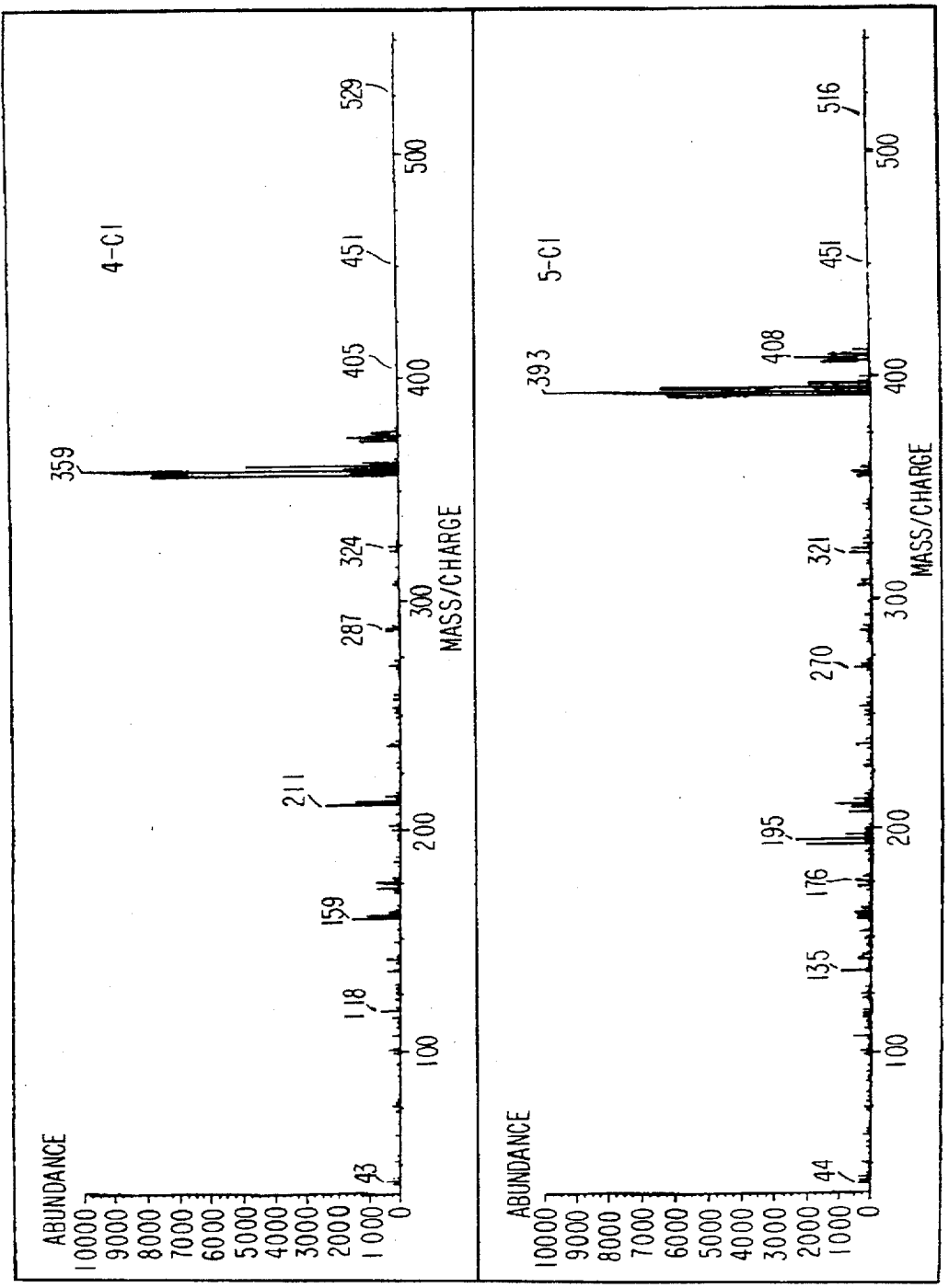
Figure 6E:
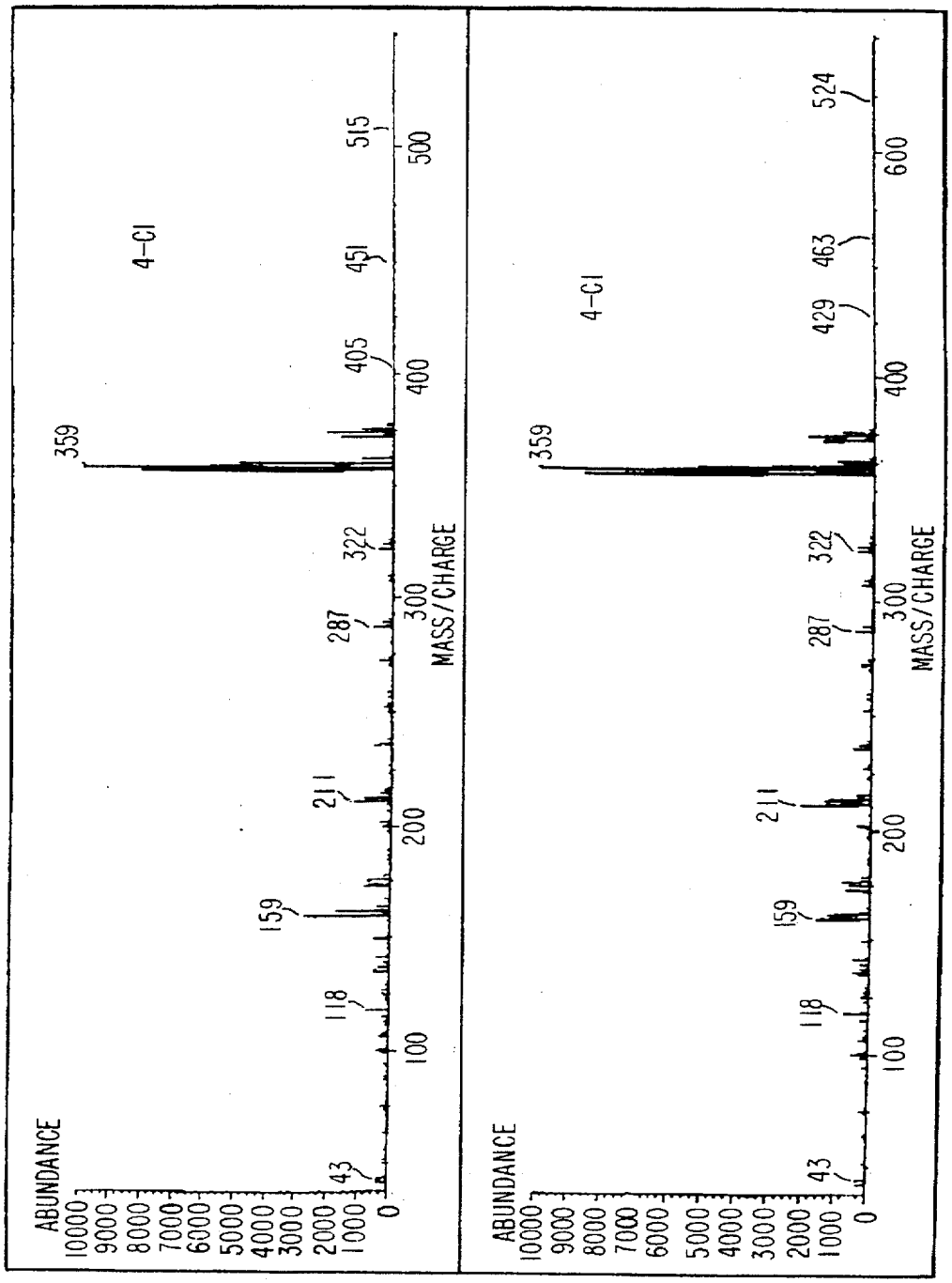
Figure 6F:
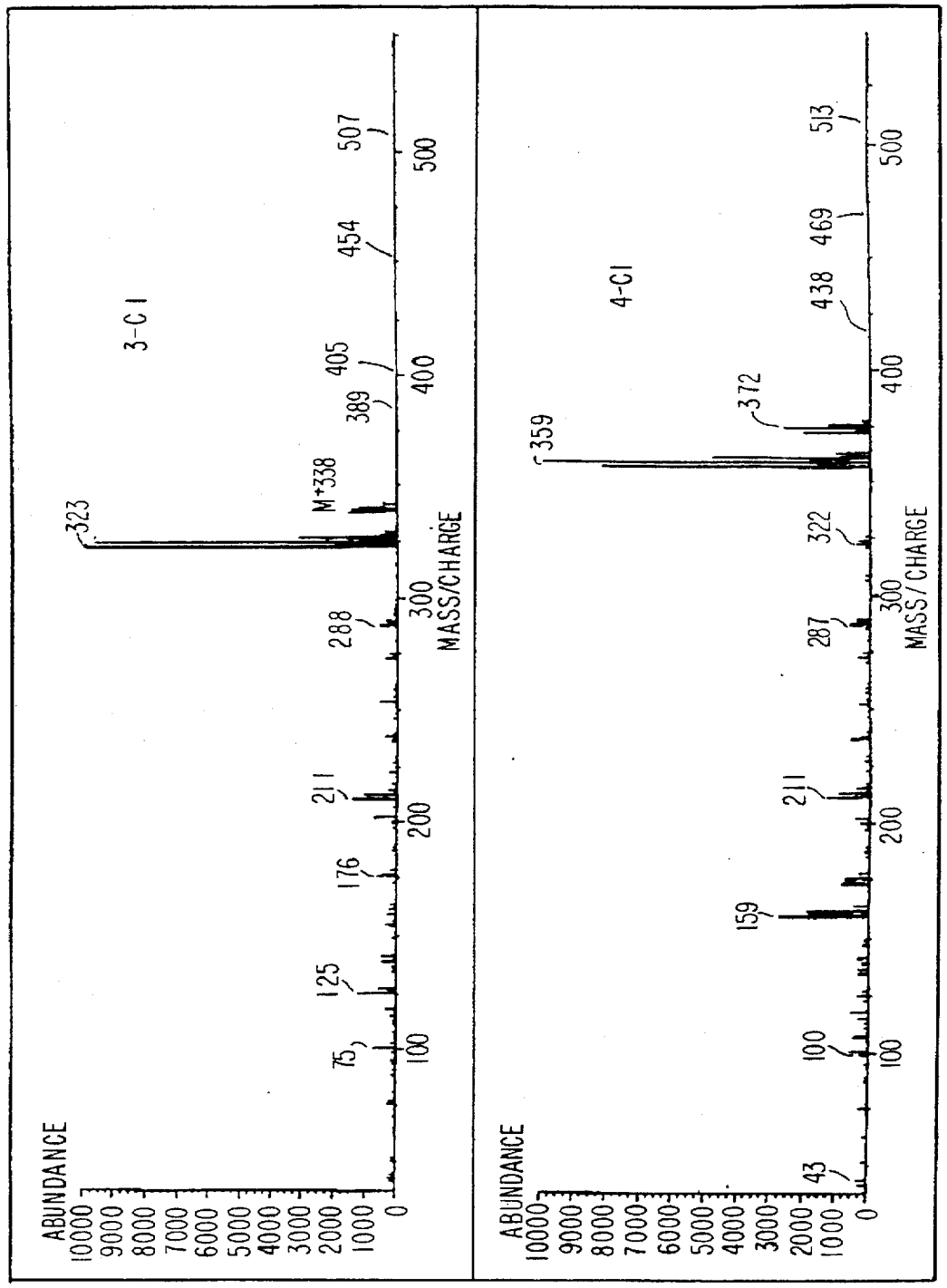
Figure 7:
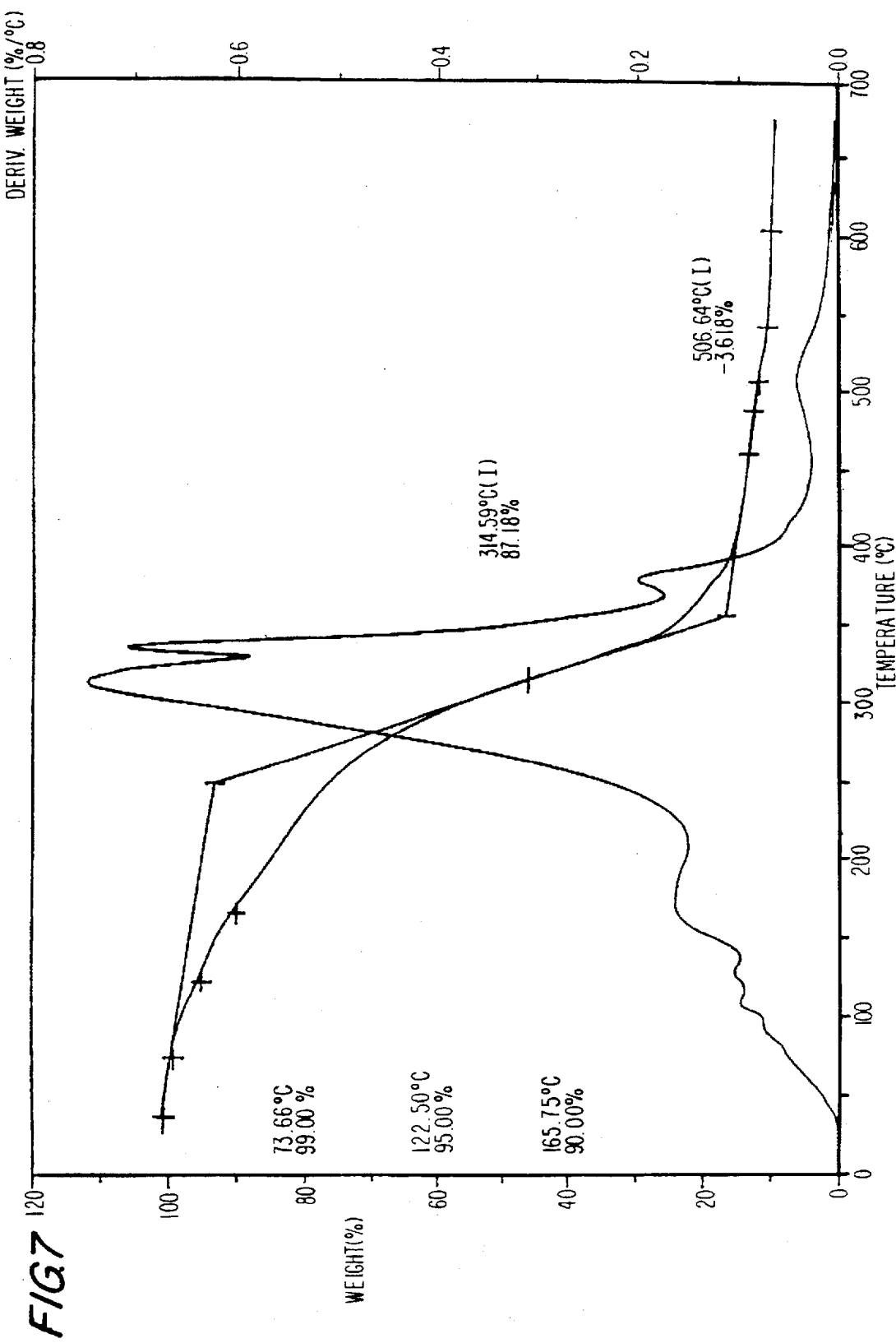

The GC/MS (FIGS. 5 & 6) spectrum reveals many peaks which were attributed to different isomers of partially chlorinated TMPIs: peaks between r.t. of 12.25 to 17.14 min. were identified (% area) as one trichlorinated isomer (3.1%; Mw 338), seven tetrachlorinated isomers (with a total of 50.3%; Mw 372) and eight pentachlorinated isomers (with a total of 37.4%; Mw 406). Small peaks (the remaining 10%; area %) are observed at r.t. 17.5–22. min. and are assigned to hexa- hepta and octa- isomers (i.e. the peak 19.5 min. was identified as a hexachlorinated TMPI, Mw 440). TGA (FIG. 7): 5% at 122° C., 10% at 166° C. and a major peak at 315° C.

Figure 8:
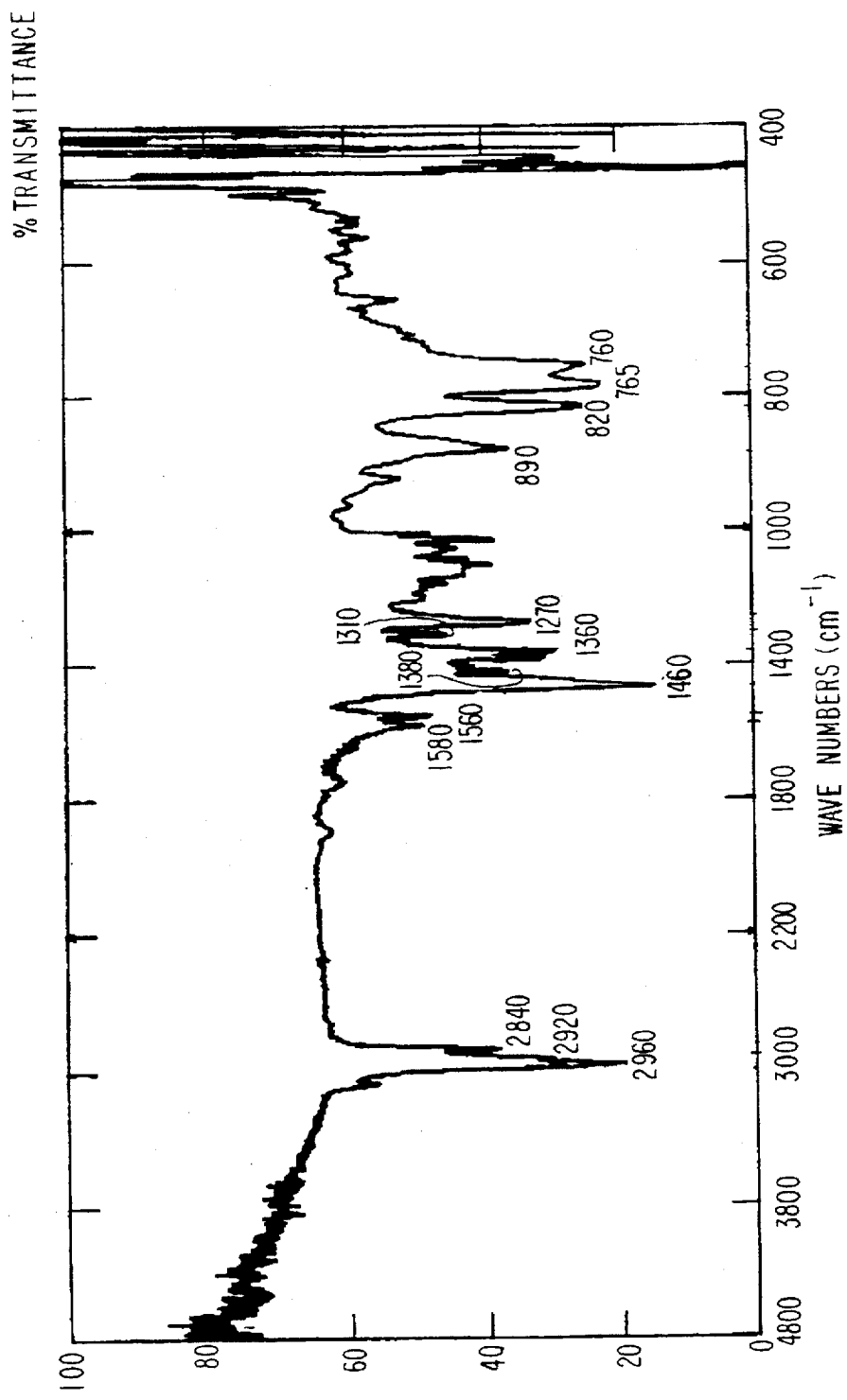

IR (FIG. 8; $cm^{-1}$): 2960, 2920, 2840, 1580, 1560, 1460, 1380, 1360, 1310, 1270, 890, 785, 760.

Figure 9:
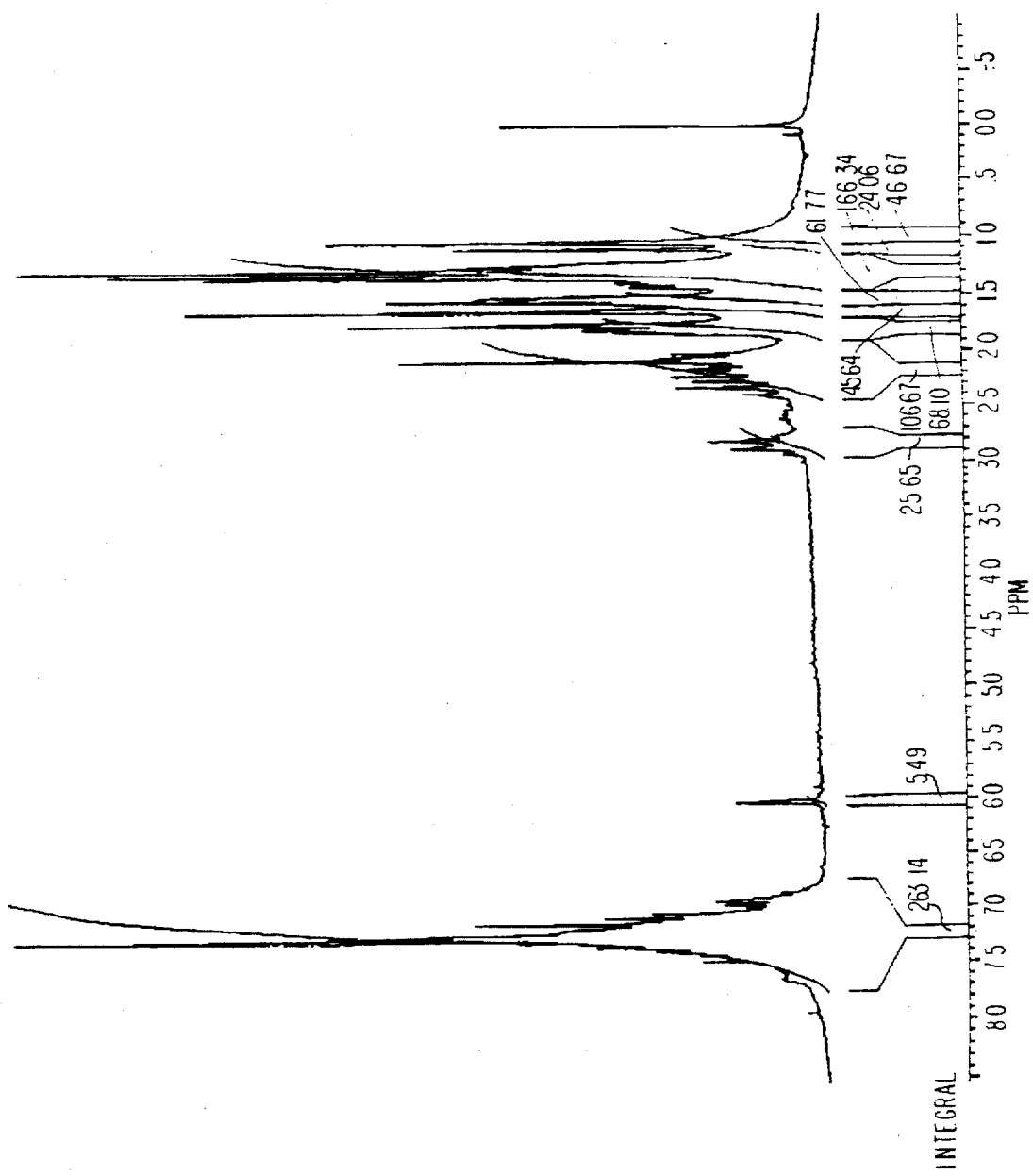

$^1$H NMR (FIG. 9; δ, in $CDCl_3$); the spectrum is very complex due to the presence of many isomers in the sample (GC/MS analysis). Three main groups of chemical shifts are characteristic of a halogenated TMPI: aromatic hydrogens observed as different singlets (between δ 7 and 8 ppm); the methylenic hydrogens of the cyclopentane ring of the indan observed as AB quartets between δ 2 and 3 pm; and the methyl groups appearing as sharp peaks between δ 1 and 2 ppm.

Figure 10:
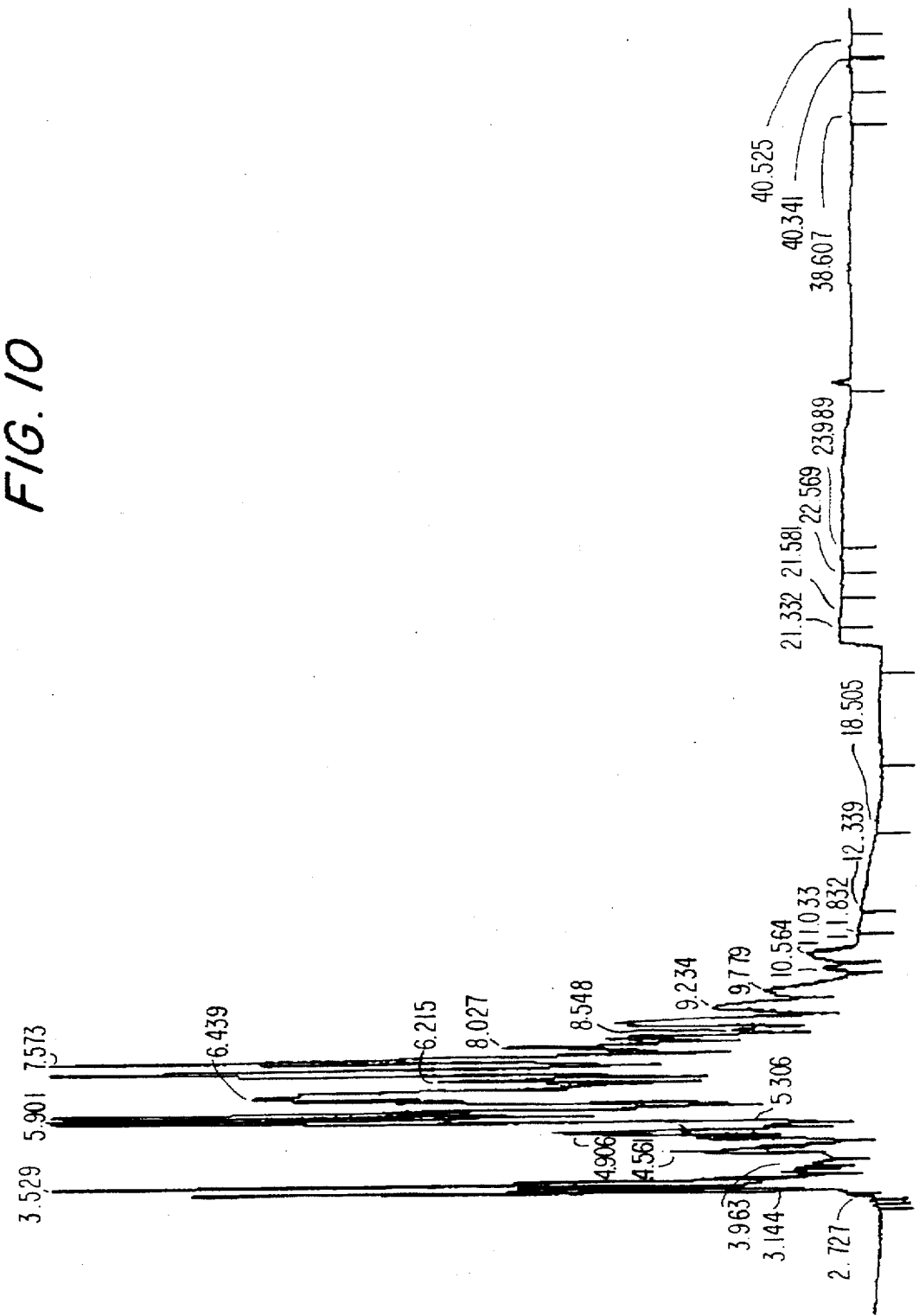

The HPLC chromatogram is shown in FIG. 10.

EXAMPLE 3

Preparation of Octabromotrimethylphenyl Indan (OBTMPI)

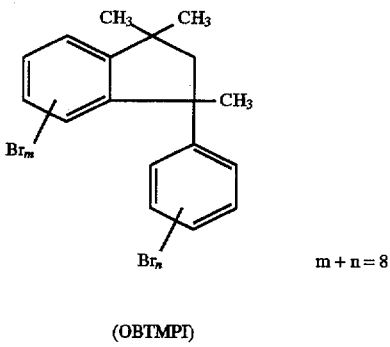

(OBTMPI)

Figure 11:
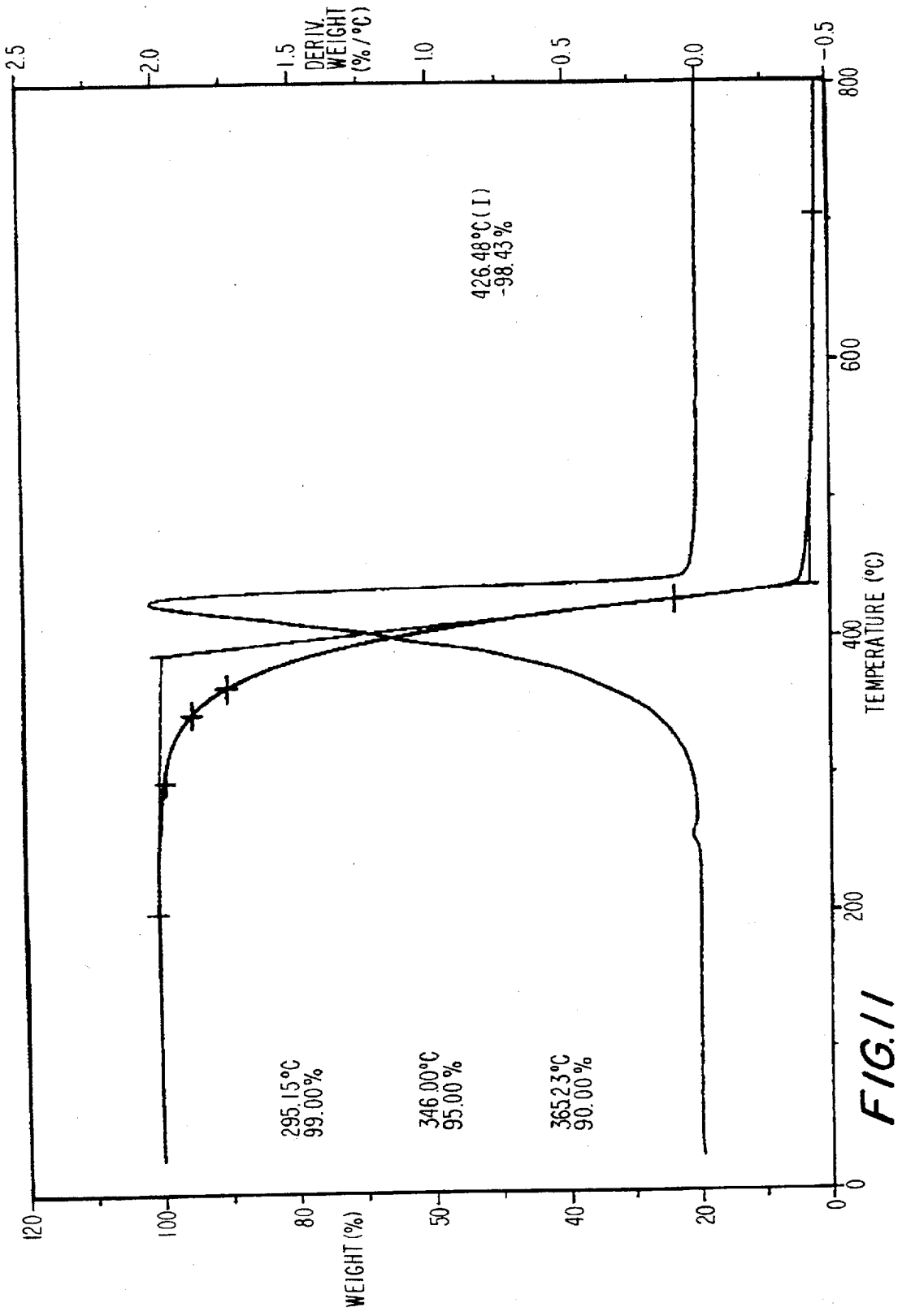
Figure 12:
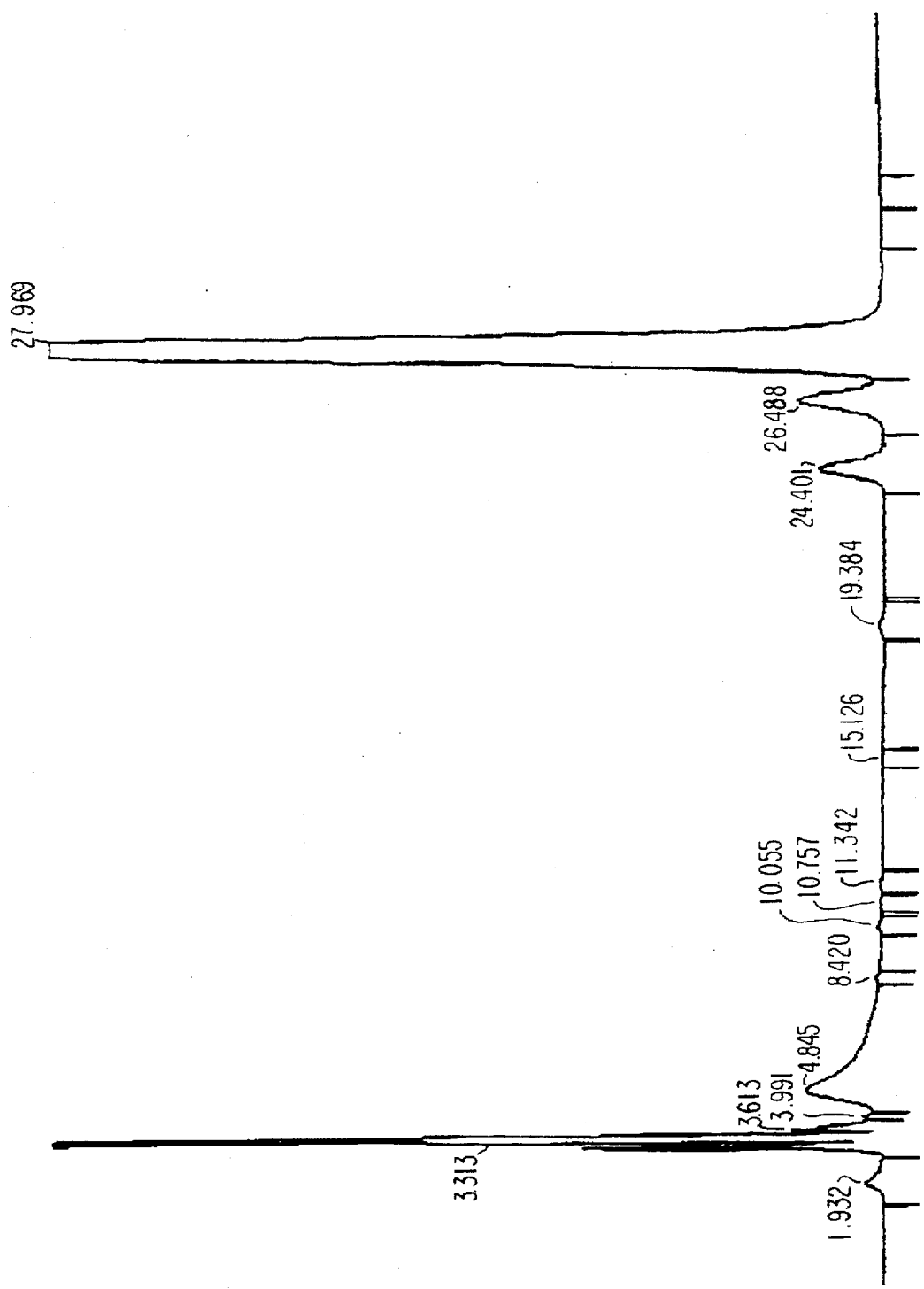
Figure 13:
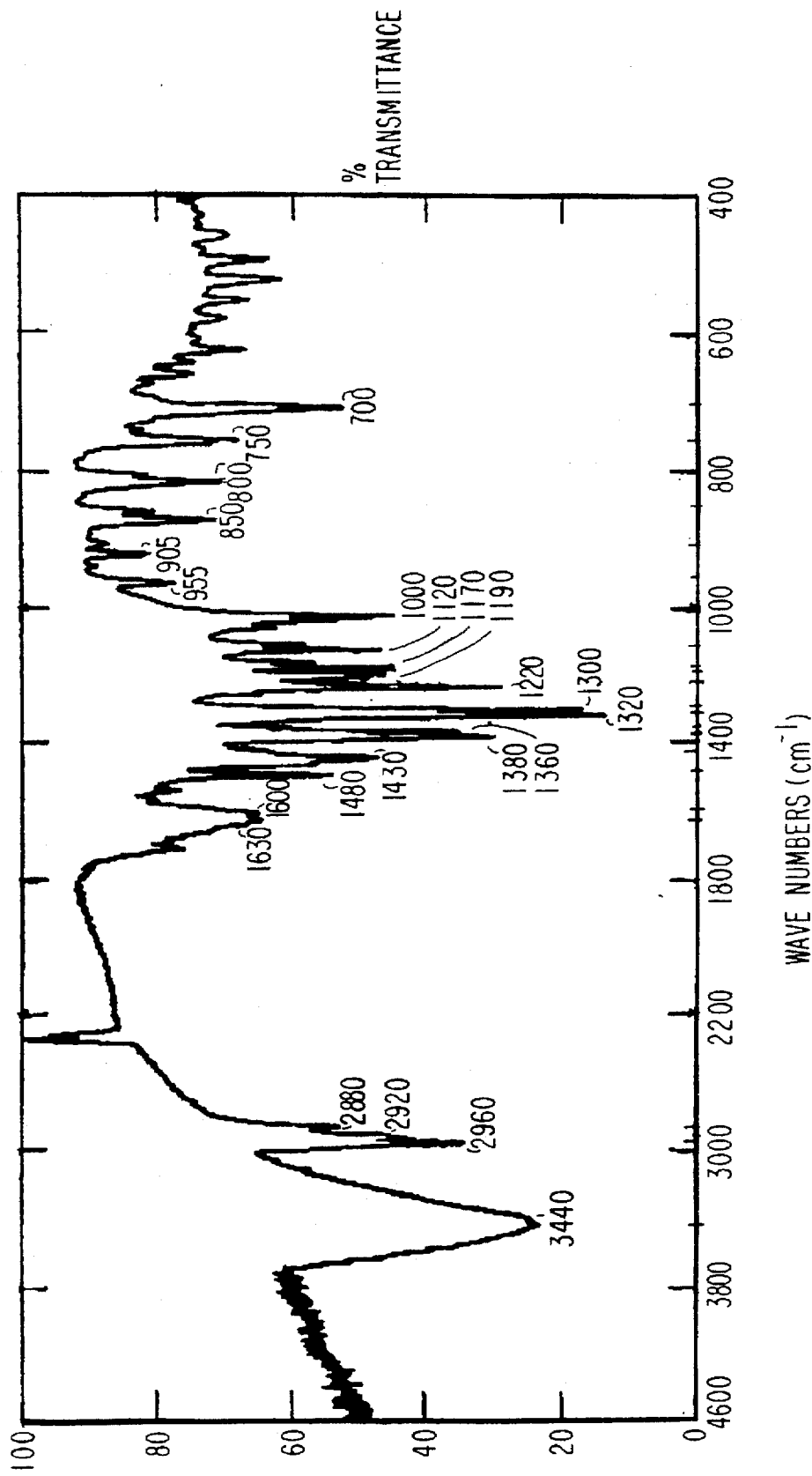
Figure 14:
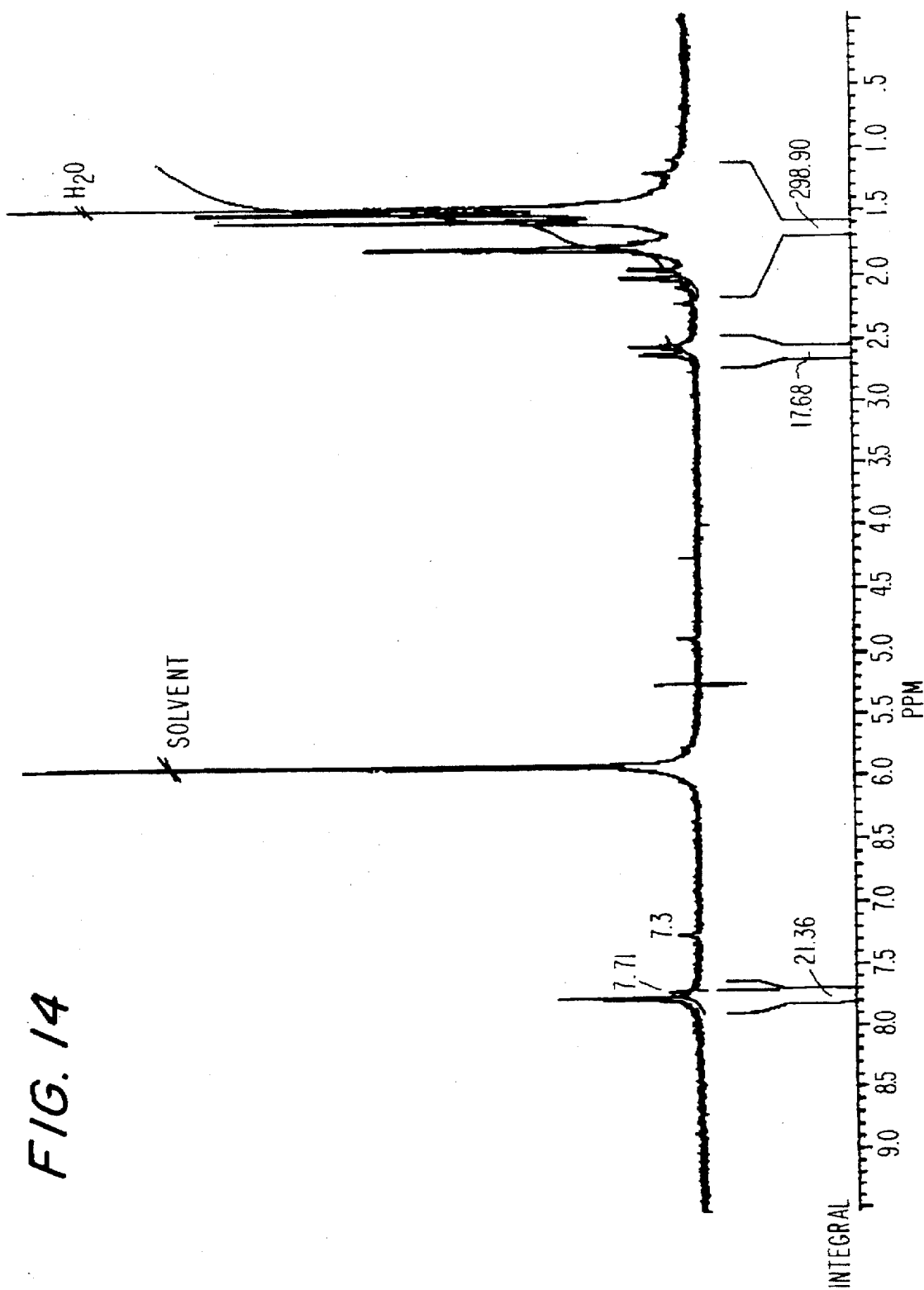

This preparation is carried out in two cycles.
First Cycle:

Into a 3-necked flask (5 liter) equipped with a mechanical stirrer, a reflux condenser and a thermocouple, were added $Br_2$ (1619 g; 10.1 mol); Fe (7.7 g; 0.14 mol) and dibromomethane (DBM, 2938 g; 1906 ml). A solution of TMPI in DBM [9.5% of 2732 g; (259.6 g TMPI; 1.1 mol)], was added dropwise to the stirred suspension at 25°–40° C., during 3.5 hrs, (the released HBr was trapped in aqueous NaOH). Mixing was continued for another 2.5 hrs at 40°–75° C. Another portion of Fe (4.4 g; 78.7 mmol) was added to the reaction mixture one hour before the end of the reaction. Water was added, to wash out the iron salts. The aqueous phase was removed. The organic layer was treated with aq. $Na_2S_2O_5$, filtered, washed with water, neutralized with $Na_2CO_3$ solution, washed again with water, with 800 ml acetone and then dried. An off-white solid (500 g) was obtained. The DBM layer, dried with anhydrous $Na_2SO_4$, was kept for the next cycle (4997 g. containing 6.7% solid).
Crystallization The product (500 g) was dissolved in hot toluene (2250 ml), treated with active carbon (10 g) and cooled. The precipitate (after cooling) was filtered, washed with acetone and dried. A slightly yellow solid was isolated (352 g), m.p. 248.6° C. Elementary analysis calculated for $C_{18}H_{12}Br_8$: C 24.9; H 1.4; Br 73.7%. Found: C 25.6; H 1.3; Br 73.0%. TGA (FIG. 11) 1/5%=296°/346° C., 10% =365° C. and the major peak at 426° C. HPLC (FIG. 12): 3 peaks at 24.4, 26.5 and 28 min. with 3.7, 5.4 and 90.6% ratio, respectively. The major peak is assigned to the octabromo-derivative. IR (FIG. 13; KBr; $cm^{-1}$): 3440, 2960, 2920, 2880, 1630, 1600, 1480, 1430, 1380, 1360, 1320, 1300, 1220, 1190, 1170, 1120, 1000, 955, 905, 850, 800, 750, 700. $^1$H NMR (FIG. 14; TCE; δ): 1.50 ppm ($CH_3$; s; 3H); 1.57 ppm ($CH_3$; s; 3H); 1.78 ppm ($CH_3$; s; 3H); AB quartet centered at 2.27 ppm ($CH_2$, 2H); 7.74 ppm (aromatic, s, 1H).

The concentration of the mother liquor afforded another 109 g of material of similar properties. Evaporation of the solvent to dryness left 20 g of solid.
Second Cycle The same procedure as above was carried out.

Materials used: the mother liquor from the previous run (4900 g; containing 328 g of solids); $Br_2$ (1664 g; 10.4 mol); Fe (7.7 g; 138 mmol); A solution of TMPI (260 g 1.1 mol) in DBM (840 g).

The TMPI solution was added dropwise during 2 hours at 28°–43° C. Mixing was continued (43°–78° C.) for 3 hours more. After 4.5 hrs (from the start) Fe (4.4 g; 78.8 mmol)

was added and 30 min. later Br$_2$ (10 ml) was added. The reaction was stopped when the evolution of HBr ceased (after a total of 5.5 hours).

The work-up was carried out as in the first cycle. A yellowish solid (880 g; 92.5% yield) was obtained. TGA: 1/5%=271°/338° C., 10%=363° C. and a major peak at 436° C. HPLC: 3 peaks at 23.9, 26 and 27.4 min. with a ratio of 3.8, 6.4 and 89.3%, respectively.

Crystallization

The above solid (855 g) was dissolved in hot toluene (reflux; 18% concentration, 4.7 liters) and 13 g of active charcoal were added. The precipitate was washed with toluene and with acetone. The dry solid (590 g) was obtained in 69% yield; m.p. 248.6° C. TGA: 1/5%=294°/348° C., 10%=370° C. and the major peak at 437° C. HPLC: 3 peaks at 24.6, 26.8 and 28.3 min. with a ratio of 2.7, 5.2 and 91.8%, respectively. Elementary analysis, calculated for $C_{18}H_{12}Br_8$: C 24.9; H 1.4; Br 73.7%. Found: C 25.7; H 1.4; Br 73.2%.

Concentration of the mother liquor to 20% of its weight afforded a second crop of a solid of similar properties after washing with toluene and acetone and drying (190 g; 22% yield). TGA: 1/5%=302°/346° C., 10%=365° C. and a major peak at 423° C. HPLC: 3 peaks at 24.3, 26.5 and 28 min. with a ratio of 3.6, 7.0 and 89.1%, respectively. Elementary analysis, found: C 25.4; H 1.2; Br 73.1%.

EXAMPLE 4

Preparation of Partially Brominated 1-Methyl-3-Phenylindan (MPI)

Following the procedure used in Example 1, 20.8 g. (0.1 mole) of MPI was brominated with 88 g. (0.55 mole) of bromine in a total 200 g DBM as solvent, using 1.5 g. Fe as catalyst. The isolated product (55 g.) contained 65.2% Br (calculated for $C_{16}H_{11}Br_5$, 66.3% Br).

EXAMPLE 5

Preparation of a Fire-Retarded Polyester

To 15 g of a liquid polyester (410 brand, Fiberplast Ltd.) there were added OBTMPI (73.1% Br; 1.1 g), twelve drops of a 7% cobalt octoate solution and 3 drops of methyl ethyl ketone peroxide at ambient temperature with mixing. The mixture was quickly cast into a Teflon mould containing cavities of dimensions 6×100×3 mm. Curing was performed at ambient temperature for 24 hrs and then in an oven at 100° C. for 2 hrs. The specimens were removed and left to cool and the LOI (Limiting Oxygen Index) was measured and compared with that of an identically prepared sample not containing the fire retardant compound. The LOI of the control specimen was 17.5 LOI for 5% loading (only 3.6% Br) was 19.6.

EXAMPLE 6

Application Tests With Several Thermoplastic Resins

Several resins were compounded with OBTMPI as fire retardant. The formulations (Table 1–3) were prepared in a Brabender Plasticorder, and samples for the evaluation of product performance were molded at temperatures appropriate for each resin.

The compounding and press temperatures were as follows:

| Resin | Table | Temperature of Compounding | Temperature of Molding |
|---|---|---|---|
| ABS | 1 | 220° C. | 200° C. |
| Polyamide | 2 | 260 | 250 |
| Polypropylene | 3 | 230 | 200 |
| HIPS | 4 | 230 | 200 |

The flammability and mechanical properties obtained are recorded in the tables. Their definition is as follows:

Flammability:

UL-94 vertical burning test in a flammability hood (according to UL); Limiting oxygen index (LOI) (ASTM D 2863-77) on a FTA Flammability Unit Stanton Redcroft.

Izod Notched Impact Energy:

(ASTM D 256-81) on a Pendulum impact tester type 5102 Zwick.

HDT:

Deflection temperature under flexural load (18.5 kg/cm$^2$) (ASTM D 648-72) on a CEAST 6055.

U.V. Stability:

Accelerated weathering test-irradiation for 250 hrs and measuring of the color change by color deviation, on an Accelerated Weathering Tester Q-U-V (B-lamps), (The Q-Panel Co.).

Color Deviation:

Color measurement and comparison with reference specimen, on a Spectro Color Meter SCM-90, (Techno-Instruments Ltd.).

TABLE 1

COMPARISON BETWEEN OBTMPI AND OCTABROMODIPHENYL ETHER (OCTA) IN ABS

| COMPONENTS | | |
|---|---|---|
| ABS NOVODUR P2H AT (BAYER) | 75.3 | 75.7 |
| OBTMPI | 15.8 | |
| OCTA | | 15.4 |
| ANTIMONY TRIOXIDE | 7.7 | 7.7 |
| ADDITIVES | 1.2 | 1.2 |
| PROPERTIES | | |
| BROMINE CONTENT % | 12 | 12 |
| FLAMMABILITY-UL94 (1.6 mm) | VO | VO |
| UV STABILITY-QUV (250 H), DE | 41 | 44 |
| HDT (264 psi), C | 84 | 81 |

TABLE 2

USE OF OBTMPI IN NYLON 6

| COMPONENTS % | |
|---|---|
| NYLON 6 CAPRON 8022HS (ALLIED) | 72.6 |
| OBTMPI | 19.2 |
| ANTIMONY TRIOXIDE | 6.8 |
| HOSTAFLON TF 3202 (HOECHST) | 1 |
| AC-400A (ALLIED) | 0.4 |
| PROPERTIES | |
| BROMINE CONTENT % | 15 |
| FLAMMABILITY-UL94 (1.6 mm) | VO |
| IZOD NOTCHED IMPACT, J/m | 49 |
| HDT (264 psi), C | 51 |

TABLE 3

COMPARISON BETWEEN OBTMPI AND DECABROMODIPHENYL ETHER (DECA) IN HIPS

| COMPONENTS % | | |
|---|---|---|
| HIPS VESTYRON 638 (HUELS) | 81.9 | 83 |
| OBTMPI | 13.2 | |
| DECA | | 12.2 |
| ANTIMONY TRIOXIDE | 3.8 | 3.7 |
| ADDITIVES | 1.1 | 1.1 |
| PROPERTIES | | |
| BROMINE CONTENT, % | 10 | 10 |
| FLAMMABILITY-UL94 (3.2 mm) | VO | VO |
| IZOD NOTCHED IMPACT, J/m | 52 | 48 |
| UN STABILITY-QUV (250 H) YELLOWNESS INDEX | 51 | 60 |

EXAMPLE 7

Application of Brominated Methylphenylindans As Fire Retardants in Polyurethanes The products of Examples 2 and 3 were incorporated into polyurethane foams in the following manner.

A sorbitol-based polyether polyol having an hydroxyl number of 490 mg KOH/g served in two parallel application tests. In each of the tests, 1.38 g of the polyol was mixed with 11 g of the products of Examples 2 and 3, 15.8 g of Santicizer 141 (an alkyl-aryl phosphate produced by Monsanto), 0.25 g water, 1.0 g of a silicone surfactant and 1.0 g of dimethylcyclohexylamine as catalyst. When homogeneity was observed, 15.0 g of Freon 11 were added to each mixture, which were then stirred vigorously for 45 seconds. Diphenylmethane diisocyanate (MDI, 51.2 g) was then added to each and stirring was continued for 5 seconds more. The mixtures were poured into cardboard boxes lined with wrapping paper and left to rise freely. The cream times (measured from the moment of MDI introduction) were 31 and 40 seconds, respectively, whereas the rise times were 282 and 253 seconds, respectively. The foams obtained had Limiting Oxygen Indexes of 23.3 and 23.5 versus 18.6 for the blank foam, i.e. containing no fire retardant.

EXAMPLE 8

Preparation of an Epoxy Specimen (In a 1:1 Base:Hardener Epoxy)

To 15 g of a liquid resin (Araldite-rapid; Ciba-Geigy, Nr. 92.7521) there were added the halogenated TMPI (see table), 15 g of liquid hardener (Araldite-rapid Ciba-Geigy, Nr. 92.7522) at ambient temperature with mixing. The mixture was quickly cast into a Teflon mould containing cavities of dimensions 6×100×3 mm. Curing was performed at ambient temperature for 30 min. and then in an oven at 100° C. for 2 hrs. The specimens were removed and left to cool and the LOI (Limiting Oxygen Index) was measured and compared with that of an identically prepared sample not containing the fire retardant compound. The LOI of the control specimen and of the specimens containing the halogenated compound are given below:

| % Hal. in FR | Composition of specimen Base:hardener:sample (g):(g):(g) | % Hal. in specimen | LOI |
|---|---|---|---|
| blank | 15:15:0 | 0 | 19.4 |
| 73.1 Br | 15:15:4.74 | 10 | 22.9 |
| 73.1 Br | 15:15:2.37 | 5 | 21.4 |
| 42.9 Cl | 15:15:4.55 | 10 | 20.7 |
| blank | 10:20:0 | 0 | 17.9 |
| 42.9 Cl | 10:20:4.55 | 10 | 20.6 |
| 42.9 Cl | 10:20:9.1 | 20 | 22.8 |

A number of embodiments of the invention have been described, but it will be understood that the invention can be carried out with many variations, adaptations and modifications, by persons skilled in the art, without departing from its spirit or exceeding the scope of the claims.

I claim:

1. A fire retardant compound selected from the group consisting of polybrominated 1,1,3-trimethyl-3-phenylindan (TMPI) and 1-methyl-3-phenylindan (MPI) compounds containing three or more bromine atoms per molecule.

2. A compound according to claim 1, wherein it is ring brominated.

3. A compound according to claim 1, which contains from 3 to 8 bromine atoms per molecule.

4. A compound according to claim 1, selected from the group consisting of the formula:

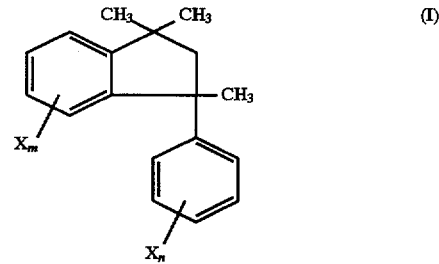

(I)

and

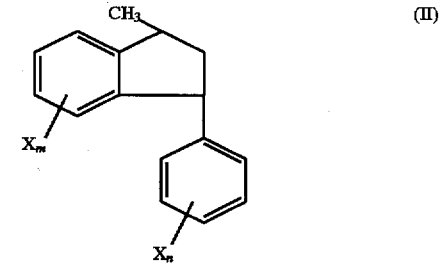

(II)

wherein X is bromine and wherein m+n is from 3 to 8.

5. A fire retarded polymeric composition comprising a polymeric base and from 0.1 to 60% by weight of at least one fire retardant compound selected from the group consisting of polyhalogenated TMPI and MPI compounds containing three or more bromine atoms per molecule.

6. A fire retarded polymeric composition according to claim 5, comprising from 1 to 40% by weight of at least one fire retardant compound as defined in claim 5.

7. A fire retarded polymeric composition according to claim 5, wherein the fire retardant additive is a mixture of fire retardant compounds as defined in claim 5.

8. A fire retarded polymeric composition according to claim 5, further comprising additional fire retardants.

9. A fire retarded polymeric composition according to claim 5, further comprising additional components selected from the group consisting of antioxidants, processing aids, UV stabilizers, fillers, smoke suppressors, synergists and pigments.

10. A fire retarded polymeric composition according to claim 9, wherein the synergists are selected from the group consisting of antimony and phosphorus compounds.

11. A fire retarded polymeric composition according to claim 10, wherein the synergists are chosen from among antimony oxides or organo-phosphates.

12. A fire retarded polymeric composition according to claim 5, wherein the polymer is selected from the group consisting of unsaturated polyesters, ABS, polyamides, polyolefins, engineering thermoplastics, polyurethanes, epoxies, high impact polystyrene (HIPS), rubbers and thermosets.

13. Fire retarded synthetic textiles, comprising a polymeric base and from 0.1 to 60% by weight of at least one compound as defined in claim 5 to a polymer base by mixing.

14. Process for preparing fire retarded polymeric compositions according to claim 5, comprising adding a compound according to claim 1 to a polymer base by mixing.

15. Process for preparing a fire retarded polymeric composition according to claim 5, comprising preparing a masterbatch comprising a compound as defined in claim 5 and blending the same with a polymer base.

16. A masterbatch comprising a compound according to claim 1 and a polymeric material.

* * * * *